(12) United States Patent
Thiruvengadam et al.

(10) Patent No.: US 7,626,045 B2
(45) Date of Patent: Dec. 1, 2009

(54) SYNTHESIS OF HIMBACINE ANALOGS

(75) Inventors: Tiruvettipuram K. Thiruvengadam, Kendall Park, NJ (US); Tao Wang, Sprinfield, NJ (US); Jing Liao, Livingston, NJ (US); John S. Chiu, Parsippany, NJ (US); David J. S. Tsai, Warren, NJ (US); Hong-Chang Lee, Livingston, NJ (US); Wenxue Wu, Princeton Junction, NJ (US); Xiaoyong Fu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/428,773

(22) Filed: Apr. 23, 2009

(65) Prior Publication Data

US 2009/0203925 A1 Aug. 13, 2009

Related U.S. Application Data

(62) Division of application No. 11/330,935, filed on Jan. 12, 2006, now Pat. No. 7,541,471.

(60) Provisional application No. 60/643,932, filed on Jan. 14, 2005.

(51) Int. Cl.
*C07D 307/92* (2006.01)
(52) U.S. Cl. .................................................... 549/299
(58) Field of Classification Search .................. 549/299
See application file for complete search history.

(56) References Cited

U.S. PATENT DOCUMENTS

| 6,063,847 | A  | 5/2000  | Chackalamannil et al. |
| 6,326,380 | B1 | 12/2001 | Chackalamannil et al. |
| 6,645,987 | B2 | 11/2003 | Chackalamannil et al. |
| 7,235,567 | B2 | 6/2007  | Wu                    |
| 7,304,078 | B2 | 12/2007 | Chackalamannil et al. |

OTHER PUBLICATIONS

Chackalamannil, S., et. al. ; "Discovery of Potent Orally Active Thrombin Receptor (Protease Activated Receptor 1 ) Antagonists as Novel Antithrombotic Agents", J.Med.Chem, Sep. 22, 2005 ; vol. 48, No. 19, pp. 5884-5887, web published Aug. 24, 2005.
Clasby, M. C., et. al.; "Discovery & Synthesis of a novel series of quinoline-based thrombin reecptor (PAR-1) Antagonists" Bioorganic and Medicinal Letters ; Mar. 15, 2006; vol. 16, No. 6; pp. 1544-1548; web published Dec. 27, 2005.
Hatayama, K., et. al.; "Production of optically active propargyl alcohol derivs.—e.g.alkoxy-hydroxy-butyne or deriv., by acylating in presence of enzyme"; Derwent; Abstract; 1996-040245; 2 pages.
Ta0, B. et. al.; "Nonenzymatic Kinetic Resolution of Propargylic Alcohols by a Planar-Chiral DMAP Derivative: Crystallographic Characterization of the Acylated Catalyst"; J. Am. Chem. Soc.; 1999; 121; pp. 5091-5092; web published May 14, 1999.

International Search Report, PCT/US2006/001208 mailed Jun. 20, 2006; 4 pages.

*Primary Examiner*—Bernard Dentz
*Assistant Examiner*—David E Gallis
(74) *Attorney, Agent, or Firm*—Patent Practitioners of Schering Corporation

(57) ABSTRACT

The present invention relates to an improved process for preparing himbacine analogs. The compounds are useful as thrombin receptor antagonists. The improved process may allow for at least one of easier purification by crystallization, easier scalability, and improved process yield on the desired enantiomer.

An example of a step in the synthesis of such a himbacine analog is as follows:

2 Claims, No Drawings

SYNTHESIS OF HIMBACINE ANALOGS

CROSS-REFERENCE TO RELATED APPLICATIONS

This application is a divisional application based on and claiming the priority of U.S. patent application Ser. No. 11/330,935, filed Jan. 12, 2006, which application is based on and claims the priority of U.S. Provisional Application Nos.: 60/643,932; 60/643,927; 60/644,464; and 60/644,428, each of which was filed Jan. 14, 2005. Each of the aforementioned applications of which priority is claimed is incorporated by reference in its entirety as if fully set forth herein.

FIELD OF THE INVENTION

This application discloses a novel process for the preparation of himbacine analogs useful as thrombin receptor antagonists. The invention disclosed herein is related to those disclosed in the co-pending patent applications corresponding to U.S. provisional application Ser. Nos. 60/643,927; 60/644,464; and, 60/644,428, all four applications having been filed on the same date.

BACKGROUND OF THE INVENTION

Thrombin is known to have a variety of activities in different cell types and thrombin receptors are known to be present in such cell types as human platelets, vascular smooth muscle cells, endothelial cells, and fibroblasts. Thrombin receptor antagonists may be useful in the treatment of thrombotic, inflammatory, atherosclerotic and fibroproliferative disorders, as well as other disorders in which thrombin and its receptor play a pathological role. See, for example, U.S. Pat. No. 6,063,847, the disclosure of which is incorporated by reference.

One thrombin receptor antagonist is compound A, and salts thereof:

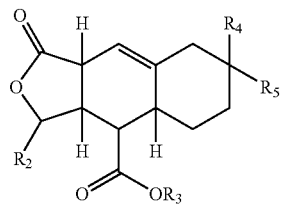

This compound is an orally bioavailable thrombin receptor antagonist derived from himbacine. Compound A may be synthesized from Compound 2A:

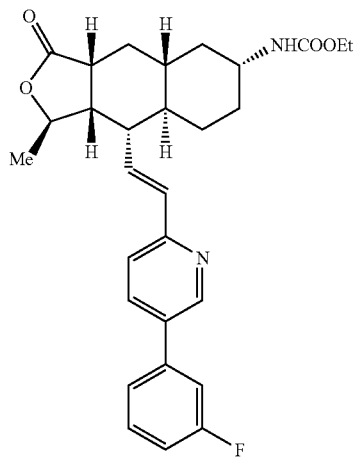

wherein $R_2$ is selected from the group consisting of alkyl, cycloalkyl, aryl, and heteroaryl and $R_3$, $R_4$ and $R_5$ are each independently selected from the group consisting of H, alkyl, cycloalkyl, aryl, arylalkyl, and heteroaryl; or, $R_4$ and $R_5$, together with the carbon atom to which they are attached, form a 5- to 7-membered ring having from 0-3 heteroatoms as ring members.

Processes for the synthesis of similar himbacine analog thrombin receptor antagonists are disclosed in U.S. Pat. No. 6,063,847, and U.S. application Ser. No. 10/412,982, and the synthesis of the bisulfate salt of a particular himbacine analog is disclosed in U.S. application Ser. No. 10/755,066, the disclosures of which are incorporated by reference herein.

SUMMARY OF THE INVENTION

The present application provides an improved process for preparing himbacine analogs from compound 2A. The improved process may allow for at least one of easier purification by crystallization, easier scalability, and improved process yield on the desired enantiomer.

One aspect of the invention is a process for preparing Compound 1:

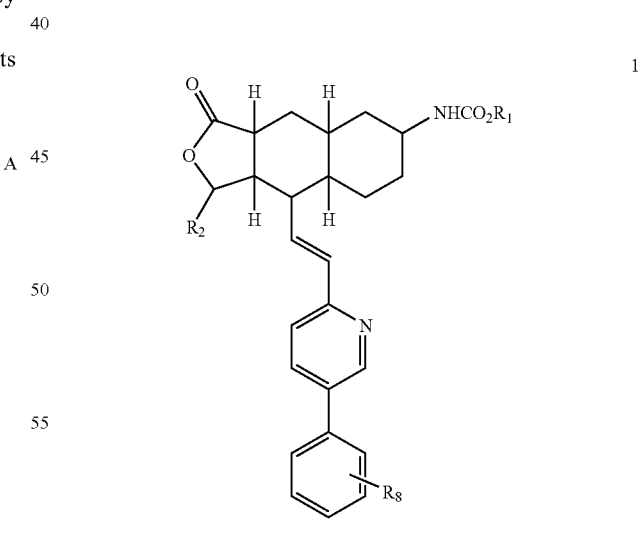

wherein $R_1$ and $R_2$ are each independently selected from the group consisting of alkyl, cycloalkyl, aryl, and heteroaryl; and $R_8$ is selected from the group consisting of halogen, $-CF_3$, $C_1$-$C_6$ alkyl, $C_1$-$C_6$ alkoxy, and $-COOR_9$, wherein $R_9$ is selected from the group consisting of H, $C_1$-$C_6$ alkyl, phenyl, and benzyl, comprising:

(a) reducing a Compound 2A:

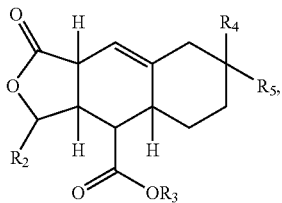
2A wherein R$_2$ is as defined above, and R$_3$ is H, alkyl, cycloalkyl, aryl, arylalkyl or heteroaryl; R$_4$ and R$_5$ are each independently selected from the group consisting of H, alkyl, cycloalkyl, aryl, arylalkyl, and heteroaryl; or, R$_4$ and R$_5$, together with the carbon atom to which they are attached, form a 5- to 7-membered ring having from 0-3 heteroatoms as ring members, to form 2B:

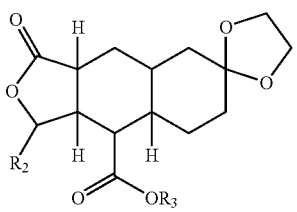
2B followed by hydrolysis of 2B to yield a compound of formula 3:

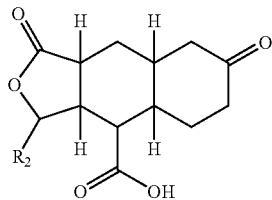
3 wherein R$_2$ is as defined above;
(b) aminating Compound 3 to yield Compound 4:

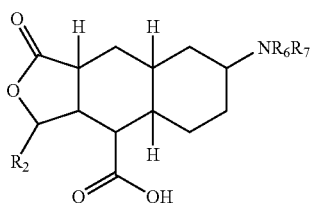
4 wherein R$_2$ is as defined above, and R$_6$ and R$_7$ are each independently selected from the group consisting of H, alkyl, cycloalkyl, aryl, and heteroaryl;

(c) converting Compound 4 to Compound 5:

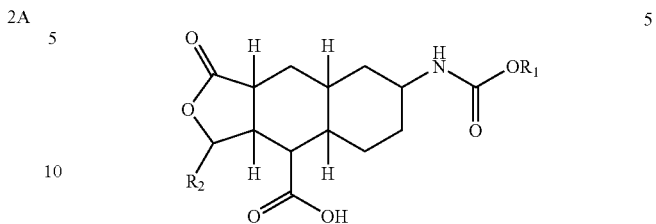
5 wherein R$_1$ and R$_2$ are as defined above;
(d) converting Compound 5 to Compound 6:

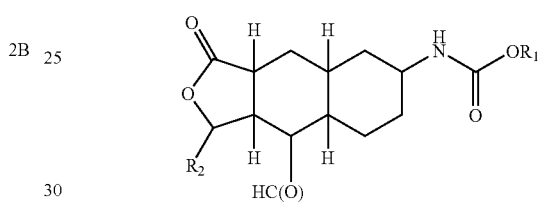
6 wherein R$_1$ and R$_2$ are as defined above; and
(e) reacting Compound 6 with compound 7:

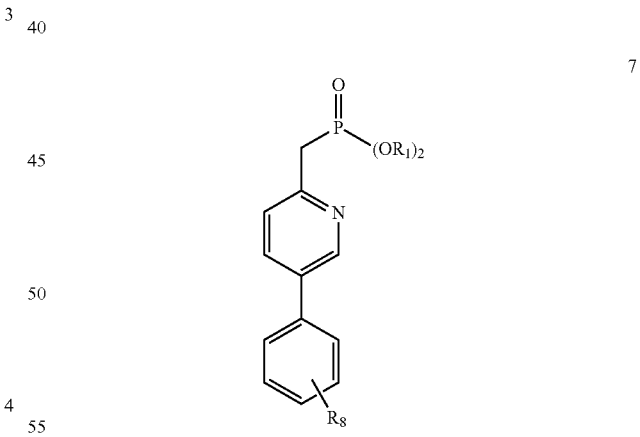
7 to prepare Compound 1. In some embodiments, Compound 7 is treated with a base, and the carbanion product is then reacted with Compound 6. Preferably, the base is an organometallic compound. More preferably, the base is an organolithium compound. Still more preferably, the base is LDA.

In some embodiments, R$_1$ is alkyl. In some embodiments, R$_1$ is ethyl. In some embodiments, R$_8$ is 3-fluoro. In some embodiments, R$_2$ is alkyl. In some embodiments, Compound 7 has the structure 7A:

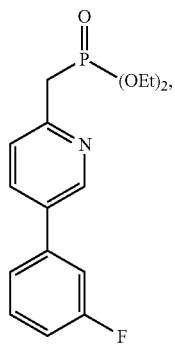

wherein said compound 7A is prepared by esterifying Compound 8:

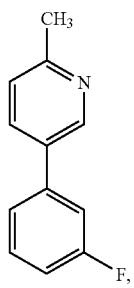

with a phosphate ester to yield Compound 7A. In some embodiments, said phosphate ester is a dialkyl halophosphate. In some embodiments, the dialkyl halophosphate is diethyl chlorophosphate. In some embodiments, Compound 8 is prepared by reacting 3-bromo-5-methylpyridine with 3-fluorophenylboronic acid.

In some embodiments, $R_2$ is methyl. In some embodiments, $R_3$ is selected from the group consisting of hydrogen, alkyl, and arylalkyl. In some embodiments, $R_3$ is arylalkyl. In some embodiments, $R_3$ is benzyl. In some embodiments, $R_4$ and $R_5$, taken together with the carbon to which they are attached, form a five-membered heterocyclic ring. In some embodiments, the five-membered heterocyclic ring contains three carbon atoms and two oxygen atoms. In some embodiments, $R_6$ and $R_7$ are each H.

In some embodiments, Compound 2A is reduced with hydrogen in the presence of a noble metal catalyst.

In some embodiments, Compound 3 is aminated with an ammonium salt in the presence of a noble metal catalyst. In some embodiments, the ammonium salt is ammonium formate. In some embodiments, the noble metal catalyst is palladium on carbon.

In some embodiments, Compound 4 is converted to Compound 5 by reacting Compound 4 with an alkyl haloformate. In some embodiments, the alkyl haloformate is an alkyl chloroformate. In some embodiments, the alkyl chloroformate is ethyl chloroformate.

In some embodiments, Compound 5 is converted to Compound 6 by reacting Compound 5 with oxalyl chloride in the presence of DMF, followed by reduction.

In some embodiments, Compound 2A is prepared by cyclizing Compound 9:

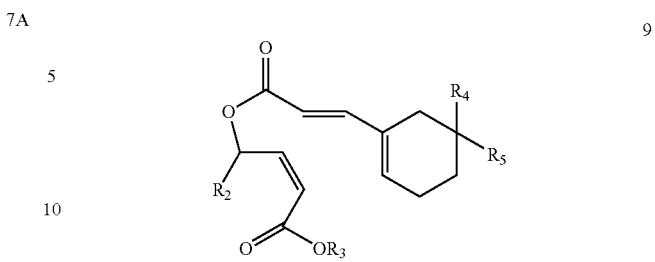

wherein $R_2$, $R_3$, $R_4$ and $R_5$ are as defined above. In some embodiments, $R_4$ and $R_5$, taken together with the hydrogen to which they are attached, form a five-membered heterocyclic ring. $R_3$ is arylalkyl. In some embodiments, $R_3$ is benzyl.

In some embodiments, the invention encompasses a process for preparing Compound A:

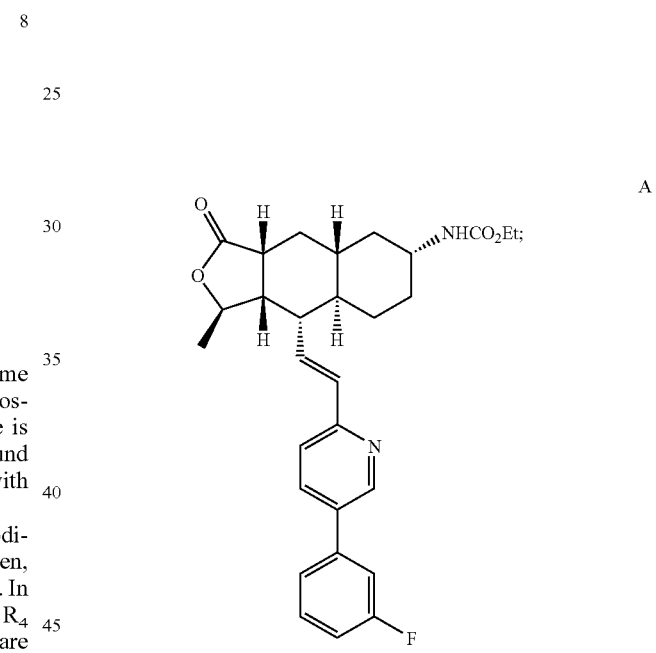

said process comprising:
(a) hydrolyzing Compound 2B:

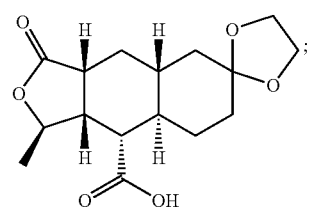

to yield Compound 3:

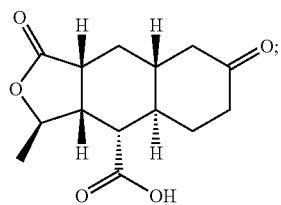

(b) aminating Compound 3 to yield Compound 4:

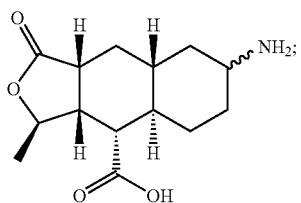

(c) converting Compound 4 to Compound 5:

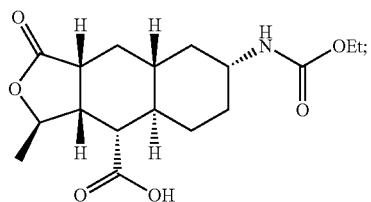

(d) converting Compound 5 to Compound 6:

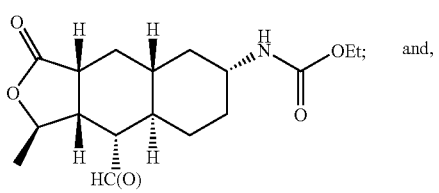

(e) converting Compound 6 to Compound A:

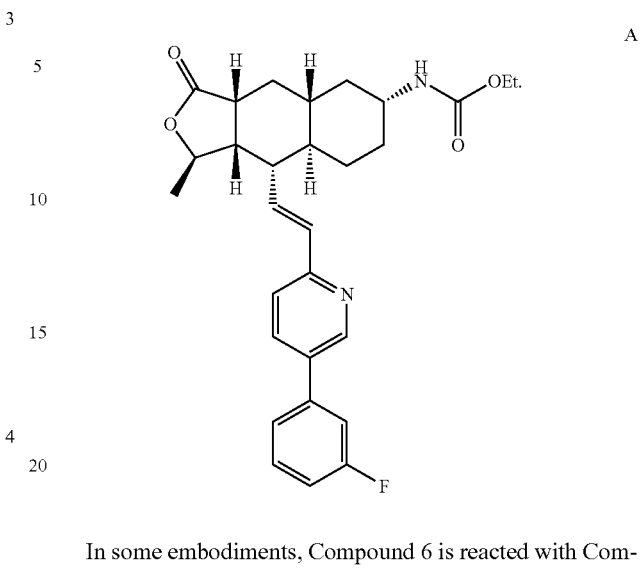

In some embodiments, Compound 6 is reacted with Compound 7A:

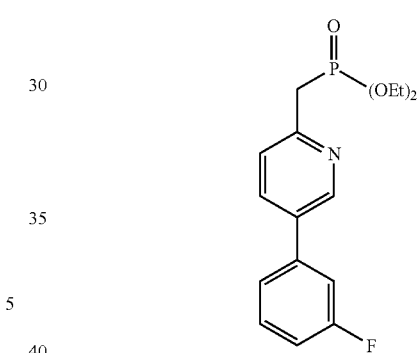

to yield Compound A. In some embodiments, Compound 7A is treated with a base, and the carbanion product is then reacted with Compound 6. In some embodiments, the base is an organometallic compound. In some embodiments, the organometallic compound is an organolithium compound. In some embodiments, the organolithium compound is LDA. In some embodiments, Compound 7A is prepared by esterifying Compound 8:

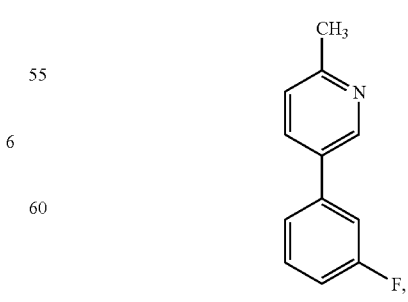

with a phosphate ester to yield Compound 7A. In some embodiments, the phosphate ester is a dialkyl halophosphate.

In some embodiments, the dialkyl halophosphate is diethyl chlorophosphate. In some embodiments, the esterification is conducted in the presence of a base. In some embodiments, the base is a dialkyl lithium amide. In some embodiments, the dialkyl lithium amide is diisopropyl lithium amide. In some embodiments, Compound 8 is prepared by reacting 3-bromo-5-methylpyridine with 3-fluorophenylboronic acid. In some embodiments, $R_1$ is alkyl. In some embodiments, $R_1$ is ethyl. In some embodiments, Compound 2B is hydrolyzed with a mineral acid. In some embodiments, Compound 3 is aminated with an ammonium salt in the presence of a noble metal catalyst. In some embodiments, the ammonium salt is ammonium formate. In some embodiments, the noble metal catalyst is palladium on carbon. In some embodiments, Compound 4 is converted to Compound 5 by reacting Compound 4 with an alkyl haloformate. In some embodiments, the alkyl haloformate is an alkyl chloroformate. In some embodiments, the alkyl chloroformate is ethyl chloroformate. In some embodiments, Compound 5 is converted to Compound 6 by reacting Compound 5 with oxalyl chloride in the presence of DMF, followed by hydrogenation in the presence of tert-amine. In some embodiments, Compound 2B is prepared by cyclizing Compound 9:

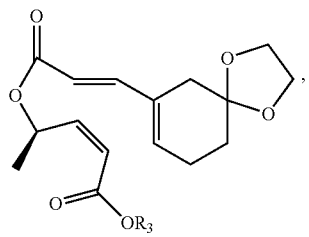

9 wherein $R_3$ is as defined above. In some embodiments, $R_3$ is arylalkyl. In some embodiments, $R_3$ is benzyl.

In some embodiments, Compound 1 is further reacted with an organic or inorganic acid to form a pharmaceutically acceptable salt. In some embodiments, the acid is selected from the group consisting of hydrochloric, sulfuric, phosphoric, acetic, citric, oxalic, malonic, salicylic, malic, fumaric, succinic, ascorbic, maleic, and methanesulfonic acids. In some embodiments, the pharmaceutically acceptable salt is the bisulfate salt.

Another aspect of the invention is a novel compound 3:

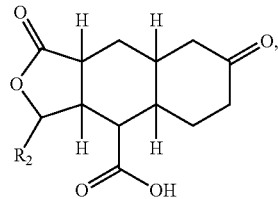

3 wherein $R_2$ is selected from the group consisting of alkyl, cycloalkyl, aryl, and heteroaryl.

Another aspect of the invention is a novel compound 4:

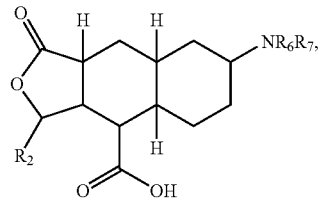

4 wherein $R_2$ is selected from the group consisting of alkyl, cycloalkyl, aryl, and heteroaryl, and $R_6$ and $R_7$ are each independently selected from the group consisting of H, alkyl, cycloalkyl, aryl, and heteroaryl.

Still another aspect of the present invention is a novel compound of the following formula:

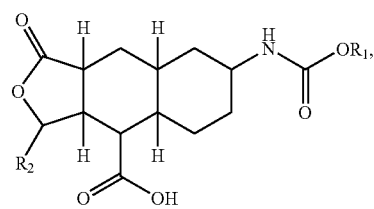

5 wherein $R_1$ and $R_2$ are each independently selected from the group consisting of alkyl, cycloalkyl, aryl, and heteroaryl, and $R_1$ is selected from the group consisting of alkyl, cycloalkyl, aryl, and heteroaryl.

In some embodiments, the invention encompasses any of the following compounds:

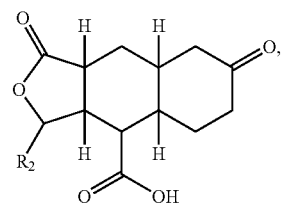

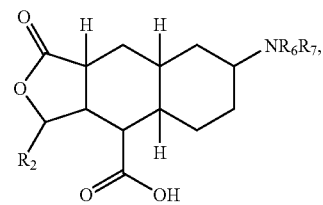

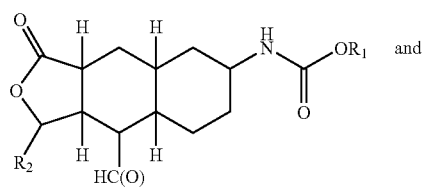

and

-continued

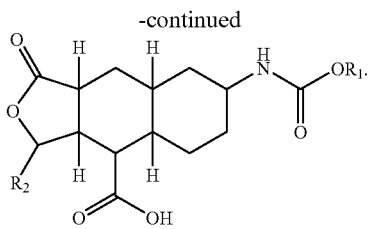

A further understanding of the invention will be had from the following detailed description of the invention.

DETAILED DESCRIPTION OF THE INVENTION

The following definitions and terms are used herein or are otherwise known to a skilled artisan. Except where stated otherwise, the definitions apply throughout the specification and claims. Chemical names, common names and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (two or more terms that are combined to identify a single moiety) to a subject structure is through the last named term of the multiple term substituent. For example, a cycloalkylalkyl substituent attaches to a targeted structure through the latter "alkyl" portion of the substituent (e.g., structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)—, or —C(=O)—. One skilled in the art will be able to determine the presence or absence of double (and triple bonds) in a covalently-bonded molecule. For instance, it is readily recognized that a carboxyl functionality may be represented by —COOH, —C(O)OH, —C(=O)OH or —CO$_2$H The term "heteroatom," as used herein, means a nitrogen, sulfur or oxygen atom. Multiple heteroatoms in the same group may be the same or different.

As used herein, the term "alkyl" means an aliphatic hydrocarbon group that can be straight or branched and comprises 1 to about 24 carbon atoms in the chain. Preferred alkyl groups comprise 1 to about 15 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

The term "cycloalkyl" as used herein, means an unsubstituted or substituted, saturated, stable, non-aromatic, chemically-feasible carbocyclic ring having preferably from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, or the like.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 10 carbon atoms in the chain; and more preferably about 2 to about 6 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl, or the like. If desired, the carbocyclic moiety can be substituted with from one to five, preferably, one to three, moieties, such as mono- through pentahalo, alkyl, trifluoromethyl, phenyl, hydroxy, alkoxy, phenoxy, amino, monoalkylamino, dialkylamino, or the like.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. Mono- and polycyclic (e.g., bicyclic) heteroaryl groups can be unsubstituted or substituted with a plurality of substituents, preferably, one to five substituents, more preferably, one, two or three substituents (e.g., mono-through pentahalo, alkyl, trifluoromethyl, phenyl, hydroxy, alkoxy, phenoxy, amino, monoalkylamino, dialkylamino, or the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi (π) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, more preferably, five to seven atoms. Polycyclic ring systems consisting of two rings preferably contain from six to sixteen atoms, most preferably, ten to twelve atoms. Polycyclic ring systems consisting of three rings contain preferably from thirteen to seventeen atoms, more preferably, fourteen or fifteen atoms. Each heterocyclic ring has at least one heteroatom. Unless otherwise stated, the heteroatoms may each be independently selected from the group consisting of nitrogen, sulfur and oxygen atoms.

The terms "Hal," "halo," "halogen" and "halide," as used herein, mean a chloro, bromo, fluoro or iodo atom radical. Chlorides, bromides and fluorides are preferred halides.

The following abbreviations are defined as follows: LDA is lithium diisopropylamide; EtOH is ethanol; Me is methyl; Et is ethyl; Bu is butyl; n-Bu is normal-butyl, t-Bu is tert-butyl, OAc is acetate; KOt-Bu is potassium tert-butoxide; NBS is N-bromosuccinimide; NMP is 1-methyl-2-pyrrolidinone; DMA is N)N-dimethylacetamide; n-Bu$_4$NBr is tetrabutylammonium bromide; n-Bu$_4$NOH is tetrabutylammonium hydroxide, n-Bu$_4$NHSO$_4$ is tetrabutylammonium hydrogen sulfate, and equiv. is equivalents.

General Syntheses

The following scheme illustrates a process for preparing Compound 1 from Compound 2B:

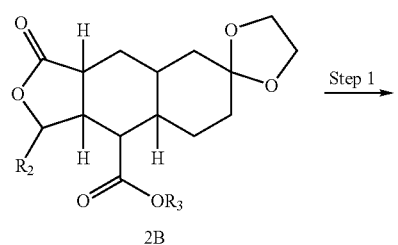

2B

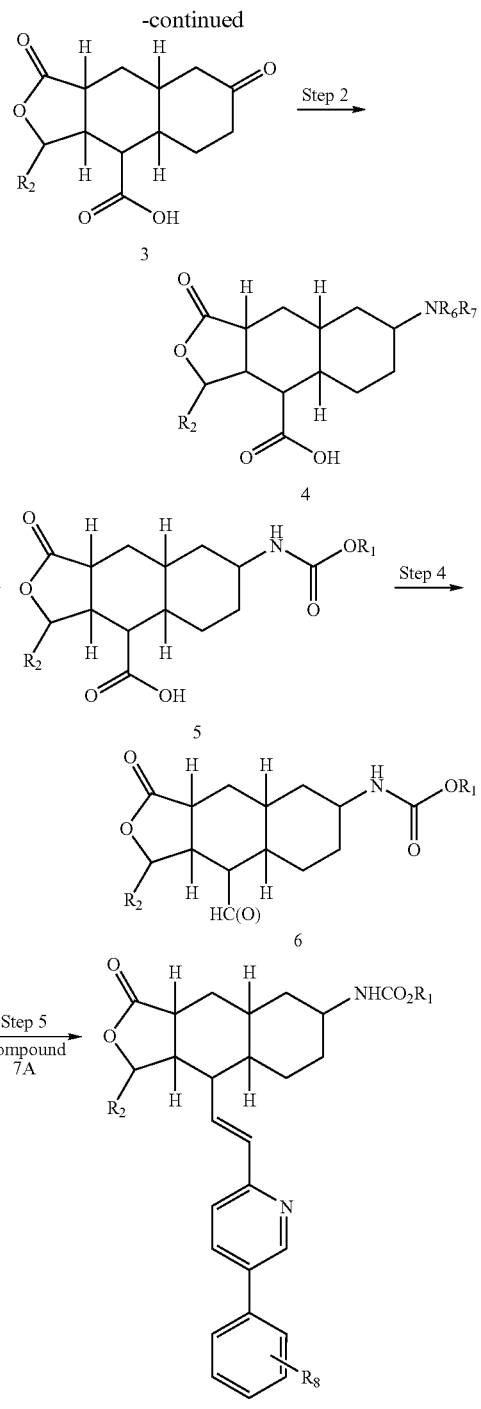

Step 1: Compound 2B may be prepared from compound 2A according to the process described in U.S. Pat. No. 6,063,847. It may be converted to Compound 3 by reaction with an acid in a solvent. Suitable acids include strong acids such as, for example, hydrochloric acid and sulfuric acid. Hydrochloric acid is preferred. The solvent may be any organic solvent that does not interfere with the reaction Acetone is a particularly preferred solvent. According to one aspect of the present invention, Compound 2B is converted to Compound 3 by reaction with 1N hydrochloric acid in acetone as solvent.

Step 2: Compound 3 is subsequently aminated, under suitable amination conditions, to yield Compound 4. The amination may be conducted with an aminating agent. According to one aspect of the invention, the aminating agent is an ammonium salt, for example ammonium formate. The amination is preferably conducted in a solvent, preferably an alcohol, for example a lower alkanol. Ethanol is preferred. Following the addition of the aminating agent, the reaction mixture is combined with a noble metal catalyst. Various noble metal catalysts are suitable, such as palladium or platinum on various types of carriers. More than one noble metal may be used as the catalyst. A preferred catalyst is palladium on an activated carbon support.

Step 3: The amine moiety of Compound 4 is then converted to the corresponding carbamate 5. The conversion may be conducted with an alkyl haloformate. Ethyl chloroformate is preferred. It may be advantageous to conduct the reaction in the presence of a base, such as a strong aqueous base. Suitable non-limiting examples of appropriate bases include the alkali metal hydroxides. Sodium hydroxide is preferred. Following completion of the reaction, Compound 5 may be isolated by crystallization.

Step 4: The carbamate acid 5 is subsequently converted to the carbamate aldehyde 6. This may be done with, for example, oxalyl chloride in the presence of a solvent. Catalytic amounts of DMF may be employed. Suitable solvents include organic solvents, for example THF. Excess oxalyl chloride is then removed, and the reaction mixture is subjected to reducing conditions. Hydrogenation conditions are preferred. Suitable hydrogenation conditions include providing hydrogen gas at a pressure ranging from 50 to 200 psi, for example 100 psi. The hydrogenation is advantageously conducted in the presence of a hydrogenation catalyst and a tert-amine such as, for example, lutidine. Such catalysts are known to those of ordinary skill in the art and include, for example, noble metals on a support. A preferred hydrogenation catalyst is palladium on activated carbon.

Step 5: The aldehyde functionality on Compound 6 is subsequently reacted with the phosphate ester 7 to yield Compound 1, as follows:

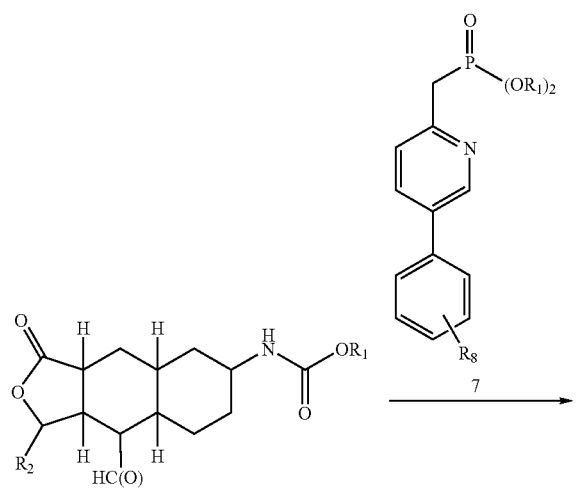

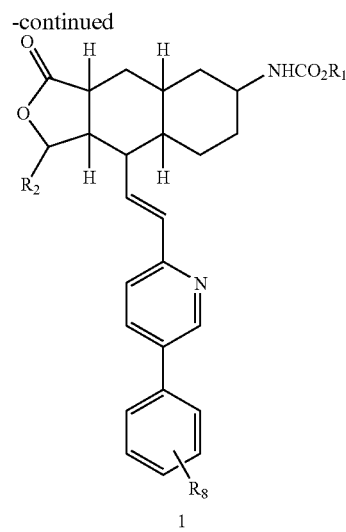

The reaction above is preferably conducted in a solvent and by treating Compound 7 with a base prior to reacting it with Compound 6. Suitable solvents include organic solvents, such as tetrahydrofuran. Preferred bases include organometallic compounds, examples of which include alkyl lithium compounds, lithium hexadimethylsilazide, sodium hexadimethylsilazide, lithium diisopropyl amide, n-butyl lithium and the like. A preferred base is LDA.

According to one aspect of the invention, the preferred phosphate ester is the following compound 7A:

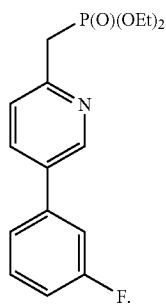

Compound 7A may be prepared from Compound 8 by treating Compound 8 with diethylchlorophosphate:

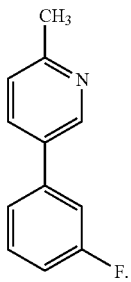

Compound 8 may be obtained by the process described by Kyoku, Kagehira et al in "Preparation of (haloaryl)pyridines," (API Corporation, Japan). Jpn. Kokai Tokkyo Koho (2004). 13 pp. CODEN: JKXXAF JP 2004182713 A2 20040702. Compound 8 is subsequently reacted with a phosphate ester, such as a dialkyl halophosphate, to yield Compound 7A. Diethylchlorophosphate is preferred. The reaction is preferably conducted in the presence of a base, such as a dialkyllithium amide, for example diisopropyl lithium amide.

Compound 1 may be further reacted with an organic acid to form a pharmaceutically acceptable salt. Suitable acids include, but are not limited to, for example, hydrochloric, sulfuric, phosphoric, acetic, citric, oxalic, malonic, salicylic, malic, fumaric, succinic, ascorbic, maleic, and methanesulfonic acids. In general, any acid capable of forming a pharmaceutically acceptable salt with Compound 1 may be suitable.

Specific Synthesis

EXAMPLE 1

Preparation of Compound 3

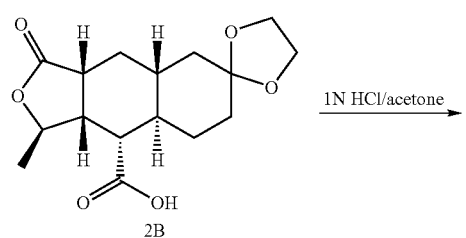

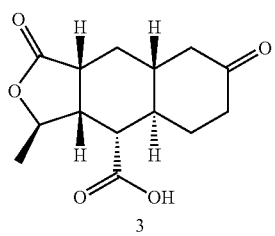

To a reactor equipped with an agitator, thermometer and nitrogen, were added about 10.5 kg of 2B, 68 L of acetone and 68 L of 1 N aqueous hydrochloric acid solution. The mixture was heated to a temperature between 50 and 60° C. and agitated for about 1 hour before cooling to room temperature. After the reaction was judged complete, the solution was concentrated under reduced pressure to about 42 L and then cooled to a temperature between 0 and 5° C. The cooled mixture was agitated for an additional hour. The product 3 was filtered, washed with cooled water and dried to provide an off-white solid (6.9 kg, yield 76%). m.p. 251° C. $^1$H NMR (DMSO) δ 12.8 (s, 1H), 4.72 (m, J=5.90 Hz, 1H), 2.58 (m, 2H), 2.40 (m, J=6.03 Hz, 2H), 2.21 (dd, J=19.0, 12.8 Hz, 3H), 2.05 (m, 1H), 1.87 (q, J=8.92 Hz, 1H), 1.75 (m, 1H), 1.55 (m, 1H), 1.35 (q, J=12.6 Hz, 1H), 1.27 (d, J=5.88 Hz, 3H). MS (ESI) M+1 m/z calcd. 267. found 267.

EXAMPLE 2

Preparation of Compound 4

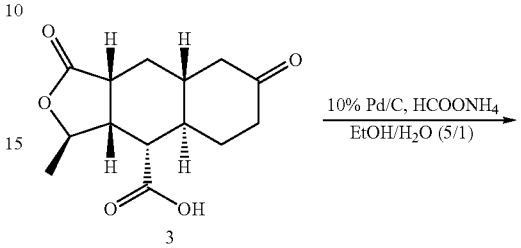

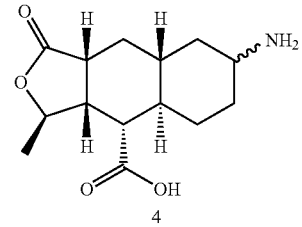

7.4 kg of ammonium formate was dissolved in 9 L of water at 15-25° C., and then cooled to 0-10° C. 8.9 kg of Compound 3 was charged at 0-15° C. followed by an addition of 89 L of 2B ethyl alcohol. The batch was cooled to 0-5° C. 0.9 kg of 10% Palladium on carbon (50% wet) and 9 L of water were charged. The batch was then warmed to 18-28° C. and agitated for 5 hours, while maintaining the temperature between 18-28° C. After the reaction was judged complete, 71 L of water was charged. The batch was filtered and the wet catalyst cake was then washed with 80 L of water. The pH of the filtrate was adjusted to 1-2 with 4N aqueous hydrochloric acid solution. The solution was used in the next process step without further isolation. The yield is typically quantitative. m.p. 216.4° C. $^1$H NMR (D$_2$O+1 drop HCl) δ 3.15 (m, 1H), 2.76 (m, 1H), 2.62 (m, 1H), 2.48 (dd, J-5.75 Hz, 1H), 1.94 (m, 2H), 1.78 (m, 2H), 1.38 (m, 2H), 1.20 (m, 6H), 1.18 (m, 1H), 0.98 (q, J=2.99 Hz, 1H).

EXAMPLE 3

Preparation of Compound 5

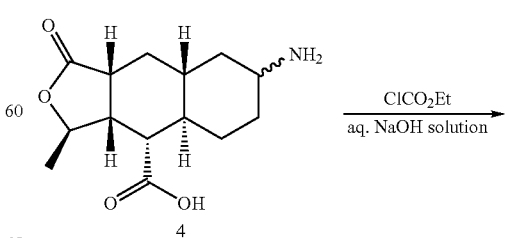

-continued

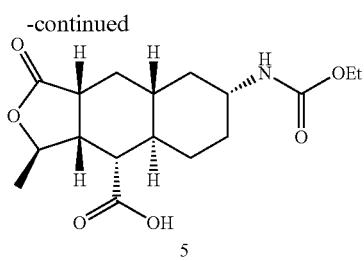

5

To a three-necked round bottomed flask equipped with an agitator, thermometer and a nitrogen inlet tube was added a solution of Compound 4 in aqueous ethanol (100 g active in 2870 ml). The solution was concentrated to about 700 ml under reduced pressure at 35° C. to 40° C. to remove ethyl alcohol. The resultant homogeneous mixture was cooled to 20° C. to 30° C. and its pH was adjusted to range from 12 to 13 with 250 ml of 25% sodium hydroxide solution while maintaining the temperature at 20-30° C. Then 82 ml of ethyl chloroformate was slowly added to the batch over a period of 1 hour while maintaining the batch temperature from 20° C. to 30° C. and aged for an additional 30 minutes. After the reaction was judged complete, the batch was acidified to pH 7 to 8 with 10 ml of concentrated hydrochloric acid (37%) and 750 ml of ethyl acetate. The pH of the reaction mixture was further adjusted to pH 2 to 3 with 35% aqueous hydrochloric acid solution. The organic layer was separated and the aqueous layer was extracted again with 750 ml of ethyl acetate. The combined organic layers were washed twice with water (200 ml). Compound 5 was isolated from the organic layer by crystallization from ethyl acetate and heptane mixture (1:1 mixture, 1500 ml) at about 70° C. to 80° C. The solid was filtered at 50° C. to 60° C., washed with heptane and then dried to provide an off-white solid (yield 50%). m.p. 197.7° C. $^1$HNMR (CD$_3$CN) δ 5.31 (brs, 1H), 4.67 (dt, J=16.1, 5.9 Hz, 1H), 4.03 (q, J=7.1 Hz, 2H), 3.41 (m, 1H), 2.55-2.70 (m, 2H), 1.87-1.92 (m, 1H), 1.32-1.42 (m, 1H), 1.30 (d, J=5.92 Hz, 3H), 1.30-1.25 (m, 6H), 0.98 (qt, J=15.7, 3.18 Hz, 2H). MS (ESI) M+1 m/z calculated 340, found 340.

EXAMPLE 4

Preparation of Compound 7A

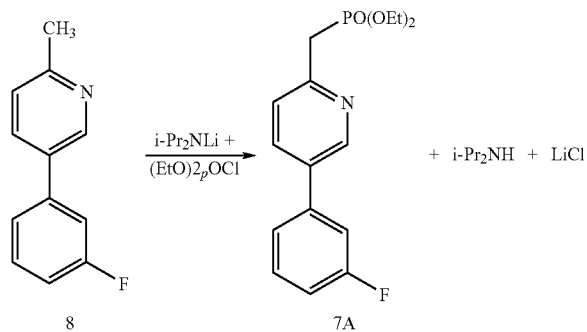

To a 10 L three-necked round bottomed flask equipped with an agitator, thermometer and a nitrogen inlet tube, was added 200 g of Compound 8 (1.07 mol, from Synergetica, Philadelphia, Pa.). THF (1000 mL) was added to dissolve Compound 8. After the solution was cooled to −80° C. to −50° C., 2.0 M LDA in hexane/THF (1175 mL, 2.2 eq) was added while maintaining the batch temperature below −50° C. After about 15 minutes of agitation at −80° C. to −50° C., diethyl chlorophosphate (185 mL, 1.2 eq) was added while maintaining the batch temperature below −50° C. The mixture was agitated at a temperature from −80° C. to −50° C. for about 15 minutes and diluted with n-heptane (1000 mL). This mixture was warmed up to about −35° C. and quenched with aqueous ammonium chloride (400 g in 1400 mL water) at a temperature below −10° C. This mixture was agitated at −15° C. to −10° C. for about 15 minutes followed by agitation at 15° C. to 25° C. for about 15 minutes. The aqueous layer was split and extracted with toluene (400 mL). The combined organic layers were extracted with 2N hydrochloric acid (700 mL) twice. The product-containing hydrochloric acid layers were combined and added slowly to a mixture of toluene (1200 mL) and aqueous potassium carbonate (300 g in 800 mL water) at a temperature below 30° C. The aqueous layer was extracted with toluene (1200 mL). The organic layers were combined and concentrated under vacuum to about 600 ml and filtered to remove inorganic salts. To the filtrate was added n-heptane (1000 ml) at about 55° C. The mixture was cooled slowly to 40° C., seeded, and cooled further slowly to −10° C. The resulting slurry was aged at about −10° C. for 1 h, filtered, washed with n-heptane, and dried under vacuum to give a light brown solid (294 g, 85% yield). m.p. 52° C. (DSC onset point). $^1$H NMR (CDCl$_3$) δ 8.73 (d, J=1.5 Hz, 1H), 7.85 (dd, J$_1$=8.0 Hz, J$_2$=1.5 Hz, 1H), 7.49 (dd, J$_1$=8.0 Hz, J$_2$=1.3 Hz, 1H), 7.42 (m, 1H), 7.32 (d, J=7.8 Hz, 1H), 7.24 (m, 1H), 7.08 (dt, J$_1$=8.3 Hz, J$_2$=2.3 Hz, 1H), 4.09 (m, 4H), 3.48 (d, J=22.0 Hz, 2H), 1.27 (t, J=7.0 Hz, 6H). MS (ESI) for M+H calcd. 324. found 324.

EXAMPLE 5

Preparation of Compound 6

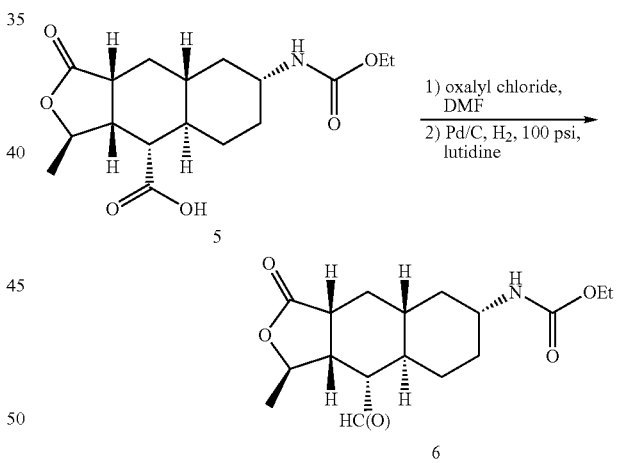

To a three-neck flask equipped with an agitator, thermometer and nitrogen inert were added the crude product solution of Compound 5 (containing about 31 g. of Compound 5 in 300 mL solution) and anhydrous DMF (0.05 mL). After the mixture was agitated for 5 minutes, oxalyl chloride (12.2 mL) was added slowly while maintaining the batch temperature between 15 and 25° C. The reaction mixture was agitated for about an hour after the addition and checked by NMR for completion of reaction. After the reaction was judged complete, the mixture was concentrated under vacuum to 135 mL while maintaining the temperature of the reaction mixture below 30° C. The excess oxalyl chloride was removed completely by two cycles of vacuum concentration at below 50° C. with replenishment of toluene (315 mL) each time, resulting in a final volume of 68 mL. The reaction mixture was then cooled to 15 to 25° C., after which THF (160 mL) and 2,6-lutidine (22 mL) were added. The mixture was agitated for 16 hours at 20 to 25° C. under 100 psi hydrogen in the presence of dry 5% Pd/C (9.0 g). After the reaction was judged complete, the reaction mixture was filtered through celite to remove catalyst. More THF was added to rinse the hydrogenator and catalyst, and the reaction mixture was again filtered through celite. Combined filtrates were concentrated under vacuum at below 25° C. to 315 mL. MTBE (158 mL) and 10% aqueous solution of phosphoric acid (158 mL) were added for a thorough extraction at 10° C. to remove 2,6-lutidine. Then phosphoric acid was removed by extracting the organic layer with very dilute aqueous sodium bicarbonate solution (about 2%), which was followed by a washing with dilute brine. The organic solution was concentrated atmospherically to a volume of 90 mL for solvent replacement. IPA (315 mL) was added to the concentrated crude product solution. The remaining residual solvent was purged to <0.5% of THF (by GC) by repeated concentration under vacuum to 68 mL, with replenishment of IPA (315 mL) before each concentration. The concentrated (68 mL) IPA solution was heated to 50° C., to initiate crystallization. To this mixture n-heptane (68 mL) was added very slowly while maintaining the batch temperature at 50° C. The crystallizing mixture was cooled very slowly over 2.5 hours to 25° C. Additional n-heptane (34 mL) was added very slowly into the suspension mixture at 25° C. The mixture was further cooled to 20° C., and aged at that temperature for about 20 hours. The solid was filtered and washed with a solvent mixture of 25% IPA in n-heptane, and then dried to provide 19.5 g of a beige colored solid of Compound 6. (Yield: 66%) m.p. 169.3° C. $^1$H NMR (CD$_3$CN) δ 9.74 (d, J=3.03 Hz, 1H), 5.42 (br, 1H), 4.69 (m, 1H), 4.03 (q, J=7.02 Hz, 2H), 3.43 (qt, J=3.80, 7.84 Hz, 1H), 2.67 (m, 2H), 2.50 (dt, J=3.00, 8.52 Hz, 1H), 1.93 (d, J=12.0 Hz, 2H), 1.82 (dt, J=3.28, 9.75 Hz, 2H), 1.54 (qd, J=3.00, 10.5 Hz, 1H), 1.27 (d, J=5.97 Hz, 3H), 1.20 (m, 6H), 1.03-0.92 (m, 2H). MS (ESI) m/z (M$^+$+1): calcd. 324. found 324.

EXAMPLE 6

Preparation of Compound A

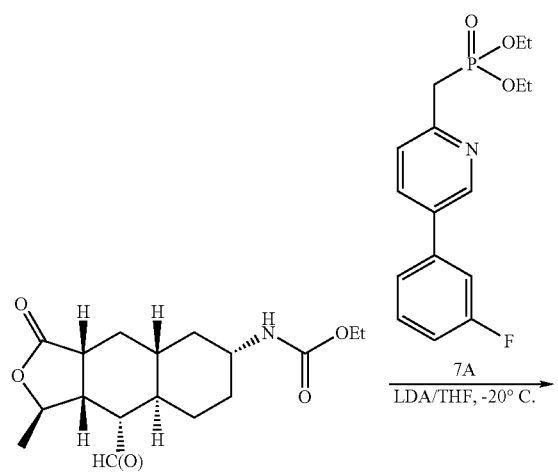

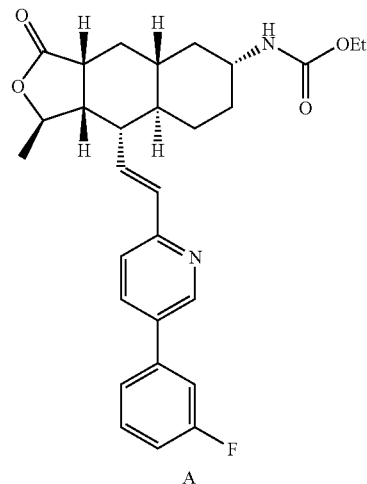

To a three-neck flask equipped with an agitator, thermometer and nitrogen inertion was added 7A (13.0 g), THF (30 mL). The mixture was cooled to below −20° C. after which lithium diisopropylamide (2M, 20 mL) was slowly added. The reaction mixture was agitated for an additional hour (Solution A). To another flask was added 6 (10.0 g) and THF (75 mL). The mixture was stirred for about 30 minutes and then slowly transferred into the solution A while maintaining the temperature below −20° C. The mixture was stirred at below −20° C. for an additional hour before quenching the reaction by adding 20 mL of water. The reaction mixture was warmed to 0° C. and the pH was adjusted to about 7 by addition of 25% H$_2$SO$_4$ (11 mL). The mixture was further warmed to 20° C. and then diluted with 100 mL of ethyl acetate and 70 mL of water. The two phases that had formed were separated and the aqueous layer was extracted with 50 mL of ethyl acetate. The solvents THF and ethyl acetate were then replaced with ethanol, and the Compound A was precipitated out as a crystalline solid from ethanol with seeding at 35 to 40° C. After cooling to 0° C., the suspension was stirred for an additional hour and then the product was filtered and washed with cold ethanol. The product was dried at 50-60° C. under vacuum to provide an off-white solid. Yield: 12.7 g, (90%). m.p. 104.9° C. (DSC onset point). $^1$H NMR (CDCl$_3$) δ 8.88 (d, J=2.4 Hz, 1H), 8.10 (dd, J=8.2, 2.4 Hz, 1H), 7.64 (1H), 7.61 (d, J=8.8 Hz, 1H), 7.55 (m, J=8.2, 6.2 Hz, 1H), 7.51 (d, J=8.0 Hz, 1H), 7.25 (dt, J=9.0, 2.3 Hz, 1H), 7.08 (d, J=8.0 Hz, 1H), 6.68 (dd, J=15.4, 9.4 Hz, 1H), 6.58 (d, J=9.6 Hz, 1H), 4.85 (dd, J=14.2, 7.2 Hz, 1H), 3.95 (dd, J=14.2, 7.1 Hz, 2H), 3.29 (m, 1H), 2.66 (m, J=12.0, 6.4 Hz, 1H), 2.33 (m, 2H), 1.76 (m, 4H), 1.30 (d, J=5.6 Hz, 3H), 1.19 (m, 4H), 1.14 (t, J=7.2 Hz, 3H), 0.98 (m, 2H), 0.84 (m, 1H). MS (EI) m/z: calcd. 492. found 492.

EXAMPLE 7

Preparation of an Acid Salt (Bisulfate) of Compound A

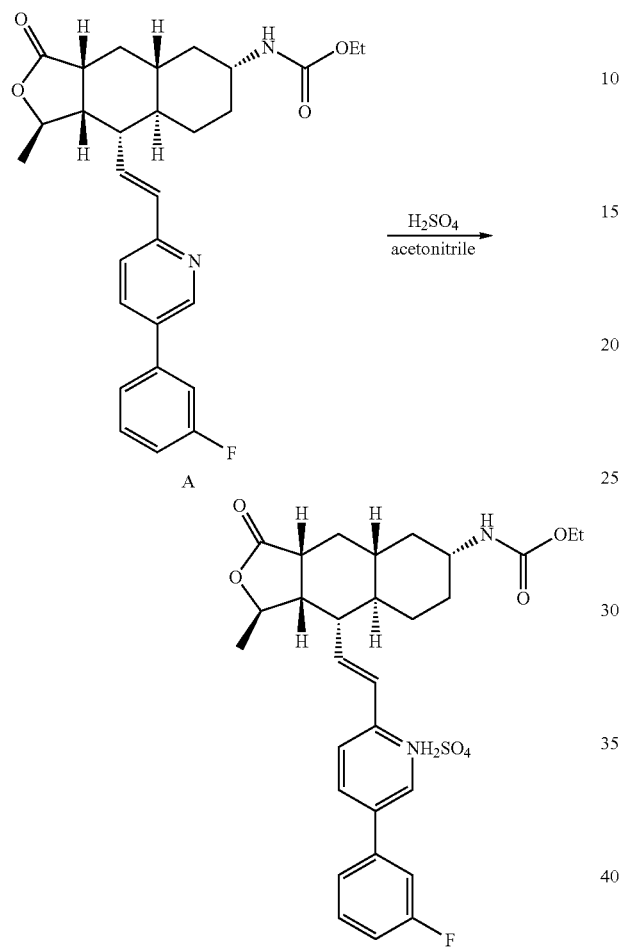

Compound A (5 g) was dissolved in about 25 mL of acetonitrile. The solution was agitated for about 10 minutes and then heated to about 50° C. About 6 mL of 2 M sulfuric acid in acetonitrile was added into the heated reaction mixture. The solid salt of Compound A precipitated out during the addition of sulfuric acid in acetonitrile. After addition of sulfuric acid solution, the reaction mixture was agitated for 1 hour before cooling to room temperature. The precipitated solid was filtered and washed with about 30 mL of acetonitrile. The wet solid was dried under vacuum at room temperature for 1 hour and at 80° C. for about 12 hours to provide about 5 g white solid (yield 85%). m.p. 217.0° C. $^1$H NMR (DMSO) 9.04 (s, 1H), 8.60 (d, J=8.1 Hz, 1H), 8.10 (d, J=8.2 Hz, 1H), 7.76 (d, J=10.4, 1H), 7.71 (d, J=7.8 Hz, 1H), 7.60 (dd, J=8.4, 1.8 Hz, 1H), 7.34 (dd, 8.4, 1.8 Hz, 1H), 7.08 (d, J=8.0 Hz, 1H), 7.02 (m, 1H), 6.69 (d, J=15.8 Hz, 1H), 4.82 (m, 1H), 3.94 (dd, J=14.0, 7.0 Hz, 2H), 3.35 (brs, 1H), 2.68 (m, 1H), 2.38 (m, 2H), 1.80-1.70 (m, 4H), 1.27 (d, J=5.8 Hz, 3H), 1.21 (m, 2H), 1.13 (t, J=7.0 Hz, 3H), 0.95 (m, 1H, 0.85 (m, 1H). MS (EI) m/z calcd. 590. found 492.

While the present invention has been described in conjunction with the specific embodiments set forth above, many alternatives, modifications and variations thereof will be apparent to those of ordinary skill in the art. All such alternatives, modifications, and variations are intended to fall within the spirit and scope of the present invention.

What is claimed is:

1. A compound of any of the following formulae:

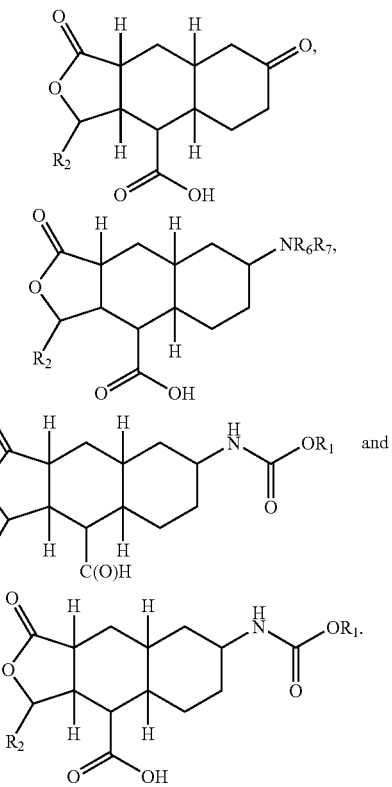

wherein $R_1$ is selected from the group consisting of alkyl, cycloalkyl, aryl, and heteroaryl, $R_2$ is selected from the group consisting of alkyl, cycloalkyl, aryl, and heteroaryl and $R_6$ and $R_7$ are each independently selected from the group consisting of H, alkyl, cycloalkyl, aryl, and heteroaryl.

2. A compound selected from the group consisting of:

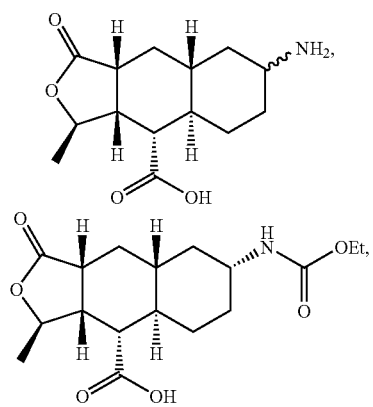

-continued
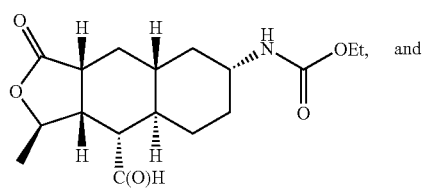 and
-continued
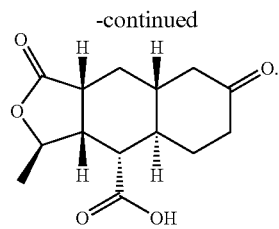
* * * * *